United States Patent [19]

Pelosi, Jr. et al.

[11] 4,162,257

[45] Jul. 24, 1979

[54] N,N-DIMETHYL-5-PHENYL-2-FURAMIDES

[75] Inventors: Stanford S. Pelosi, Jr.; Chia-Nien Yu, both of Norwich, N.Y.

[73] Assignee: Morton-Norwich Products, Inc., Norwich, N.Y.

[21] Appl. No.: 922,862

[22] Filed: Jul. 10, 1978

[51] Int. Cl.² .............................................. C07D 307/68
[52] U.S. Cl. ................................... 260/347.3; 424/285
[58] Field of Search ........................................ 260/347.3

[56] References Cited

U.S. PATENT DOCUMENTS 3,484,484  12/1969   Schwartz ........................ 260/553 A

FOREIGN PATENT DOCUMENTS 652710  11/1962  Canada .................................. 260/347.3

*Primary Examiner*—Richard Raymond
*Attorney, Agent, or Firm*—Anthony J. Franze

[57] ABSTRACT

N,N-Dimethyl-5-phenyl-2-furamides are useful as anti-inflammatory agents.

3 Claims, No Drawings

N,N-DIMETHYL-5-PHENYL-2-FURAMIDES

This invention is concerned with chemical compounds and particularly with N,N-dimethyl-5-phenyl-2-furamides of the formula:

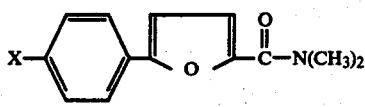

wherein X represents amino or chloro and a method for their preparation.

These compounds possess pharmacological activity. Particularly noteworthy in this respect is their utility to act as anti-inflammatory agents as evidenced by their ability to inhibit edema induced by the administration of carrageenin. Thus, when they are administered orally at a dose of 300 mg/kg suspended in a vehicle such as aqueous methyl cellulose to rats receiving carrageenin, edema resulting from that substance is inhibited [Winter et al., P.S.E.B.M. 111:544 (1962)].

The compounds of this invention can be combined in various pharmaceutical dosage forms such as capsules, tablets, dragees, suspensions and the like using excipients and adjuvants commonplace in the pharmaceutical art and with which there is no incompatibility.

The compounds of this invention are readily prepared. Currently, it is preferred to react the 5-phenyl-2-furoyl chloride wherein X represents chloro or nitro with dimethylamine in the presence of a solvent such as benzene or dioxane followed by reduction of the nitro to the amino group in the presence of palladium-on-charcoal and a solvent such as alcohol.

In order that this invention may be readily available to and understood by those skilled in the art, the following examples are supplied.

EXAMPLE I

5-(4-Chlorophenyl)-N,N-dimethyl-2-furamide

A mixture of 58 g (0.26 mole) of 5-(4-chlorophenyl)-2-furoic acid and 120 ml of thionyl chloride was heated under reflux for 3 hrs. The thionyl chloride was removed on a rotary evaporator. A small amount of benzene was added to the residual solid and then removed on a rotary evaporator. The furoyl chloride was dissolved in 300 ml of dioxane with stirring and treated dropwise with a solution of 300 ml of dioxane containing 26 g (0.58 mole) of dimethylamine, while maintaining the temperature between 15°–25°. The reaction solution was stirred at room temperature overnight and then at 80° for 4 hrs. with a small amount of solid forming. The mixture was added to 2000 ml of water and resulting solid was filtered and dried at 60° to yield 58 g (77%). An analytical sample was prepared by recrystallizing a sample from hexane, m.p. 101°–102°.

Anal. Calcd. for $C_{13}H_{12}ClNO_2$: C, 62.53; H, 4.84; N, 4.61. Found: C, 62.51; H, 4.84; N, 5.46.

EXAMPLE II

5-(4-Aminophenyl)-N,N-dimethyl-2-furamide Hydrochloride

A mixture of 56 g (0.25 mole) of 5-(4-nitrophenyl)-2-furoic acid in 130 ml of thionyl chloride was heated at reflux for 4 hrs. After slight cooling, the mixture was poured into 2 l. of hexane, with stirring, and solid separated. The solid was collected, washed with hexane and air-dried for a short period. The solid acid chloride was then added in about 20 min. to a solution of 48 g (1 mole) of dimethylamine in 500 ml of benzene. The temperature of the reaction mixture during the addition was kept under 35°, with cooling. After the addition was completed, the mixture was allowed to stir further at ambient temperature overnight. The mixture was then heated at reflux for 2 hrs. and allowed to cool. The solid was collected by filtration, washed well with benzene and air-dried. The solid was then triturated with water, filtered, dried and then recrystallized from about 2 l. of SDA-32. The yield was 42 g (65%), m.p. 173°–175°.

Anal. Calcd. for $C_{13}H_{12}N_2O_4$: C, 58.54%; H, 5.67%; N, 10.50%. Found: C, 58.68%; H, 5.74%; N, 10.49%.

A mixture of 20 g (0.077 mole) of the above compound in 750 ml of SDA-32 and 3 g of 5% Pd/C (50% water) was hydrogenated on a Parr apparatus. After theoretical hydrogen uptake, the mixture was filtered into 100 ml of ethanolic HCl solution. White crystalline solid separated gradually. The solid was collected, washed with ether and air-dried. The yield of product was 16.7 g (81%). An analytical sample melted at 228°–230° (dec.).

Anal. Calcd. for $C_{13}H_{14}N_2O_2 \cdot HCl$: C, 58.54%; H, 5.67%; N, 10.50%. Found: C, 58.68%; H, 5.74%; N, 10.49%.

What is claimed is:

1. A compound of the formula:

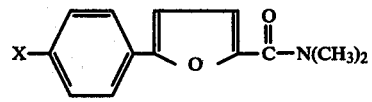

wherein X represents amino or chloro.

2. The compound 5-(4-chlorophenyl)-N,N-dimethyl-2-furamide.

3. The compound 5-(4-aminophenyl)-N,N-dimethyl-2-furamide hydrochloride.